(12) United States Patent
Reubi et al.

(10) Patent No.: US 6,866,837 B2
(45) Date of Patent: Mar. 15, 2005

(54) RADIOLABELED PEPTIDES FOR THE DIAGNOSIS AND TREATMENT OF BREAST AND PROSTATE TUMORS AND METASTASES OF SUCH TUMORS

(75) Inventors: Jean-Claude Reubi, Wabern (CH); Wout A. Breeman, Mijnsheerenland (NL); Ananthachari Srinivasan, Bedford, NH (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 10/248,668

(22) Filed: Feb. 6, 2003

(65) Prior Publication Data

US 2003/0224998 A1 Dec. 4, 2003

Related U.S. Application Data

(63) Continuation of application No. 09/485,085, filed as application No. PCT/US99/12414 on Jun. 3, 1999, now abandoned.
(60) Provisional application No. 60/088,517, filed on Jun. 8, 1998, and provisional application No. 60/088,074, filed on Jun. 5, 1998.

(51) Int. Cl.$^7$ .............................................. A61K 51/00
(52) U.S. Cl. ..................... 424/1.69; 424/1.11; 424/1.65; 424/9.1; 530/300; 530/317; 530/327
(58) Field of Search ............................... 424/1.11, 1.65, 424/9.1, 1.69; 206/223, 569, 570; 534/10–16; 530/300, 317, 327; 514/2, 14

(56) References Cited

U.S. PATENT DOCUMENTS

| 5,686,410 A | 11/1997 | Albert et al. |
| 6,200,546 B1 | 3/2001 | Hoffman et al. |

FOREIGN PATENT DOCUMENTS

| EP | 0103558 A2 | 3/1984 |
| EP | 0259904 B1 | 6/1991 |
| EP | 0243929 B1 | 9/1995 |
| WO | WO 89/02752 A1 | 4/1989 |
| WO | WO 90/03798 A2 | 4/1990 |
| WO | WO 91/01144 A1 | 2/1991 |

OTHER PUBLICATIONS

Breeman, et al., [$^{111}$In–DTPA$^0$, Pro$^1$, Tyr$^4$] bombesin: Studies In Vitro and in Rats, The Journal of Nuclear Medicine, vol. 39 (Jun. 9, 1998), p. 62P, Society of Nuclear Medicine, U.S.A. abstract No. 239.

Hoffman, Li, Sieckman, and Volkert, Uptake and Retention of a Rh–105 Labeled Bombesin Analogue in GRP Receptor Expressing Neoplasms: An In Vitro Study, The Journal of Nuclear Medicine, vol. 38 (May 1997 Supplement), pp. 188P–189P, Society of Nuclear Medicine, U.S.A. abstract No. 808.

Hoffman, Sieckman, and Volkert, Iodonated Bombesin Analogues: Effect of N–Terminal vs Side Chain Iodine Attachment on BBN/GRP Receptor Binding, The Journal of Nuclear Medicine, vol. 37 (May 1996 Supplement), p. 185P, Society of Nuclear Medicine, U.S.A. abstract No. 850.

Baidoo, et al., Synthesis and Evaluation of High Affinity Technetium Bombesin Analogs, The Journal of Nuclear Medicine, vol. 38 (May 1997 Supplement), p. 87P, Society of Nuclear Medicine, U.S.A. abstract No. 323.

Zinn, Buchsbaum, et al., Imaging Adenoviral–Mediated Gene Transfer of Gastrin Releasing Peptide Receptor (GRPr) Using a Tc–99m–Labeled Bombesin (BBN) Analogue, The Journal of Nuclear Medicine, vol. 39 (May 1998 Supplement), p. 224P–225P, Society of Nuclear Medicine, U.S.A. abstract No. 974.

Hoffman, Li, Volkert, Sieckman, Higginbotham and Ochrymowycz, Synthesis and Characterization of Rh–105 Labelled Bombesin Analogues: Enhancement of GRP Receptor Binding Affinity Utilizing Aliphatic Carbon Chain Linkers, The Jounal of Labelled Compound and Radiopharmaceuticals, vol. 40 (1997), pp. 490–492, John Wiley & Sons, Inc., U.S.A.

Breeman et al, In Vitro and In Vivo Studies of Substance P Receptor Expression in Rats with the New Analog [indium–111–DTPA–Arg1] Substance P, The Journal of Nuclear Medicine, vol. 37, (1996), p. 61P, Society of Nuclear Medicine, U.S.A.

Rogers, Curiel, Laffoon, and Buchsbaum, Synthesis and Radiolabeling of Bombesin Derivatives with Copper–64 and Binding to Cells Expressing the Gastrin Releasing Peptide Receptor, The Journal of Labelled Compounds and Radiopharmaceuticals, vol. 40 (1997), p. 482, John Wiley & Sons, Inc., U.S.A.

Safavy, Khazaeli, Qin and Buchsbaum, Synthesis of Bombesin Analogues for Radiolabeling with Rhenium–188, Cancer, vol. 80 (1997), pp. 2354–2359, American Cancer Society, U.S.A.

Rogers, et al., Tumor Localization of a Radiolabeled Bombesin Analog in Mice Bearing Human Ovarian Tumors Induced to Express GRP Receptor by an Adenoviral Vector, Cancer, vol. 80 (1997), pp. 2419–2424, American Cancer Society, U.S.A.

Rogers, Buchsbaum, et al., Localization of I–125–mIP–Des–Met14–bombesin (7–13) NH$_2$ in Ovarian Carcinoma Induced to Express GRP Receptor by an Adenoviral Vector, Cancer, vol. 80 (1997), pp. 2419–2424, American Cancer Society, U.S.A.

(List continued on next page.)

*Primary Examiner*—Dameron L. Jones
(74) *Attorney, Agent, or Firm*—Blackwell Sanders Peper Martin, LLP

(57) ABSTRACT

Compounds and methods for the diagnosis and treatment of tumors, including breast and prostate tumors and metastases thereof using radiolabelled peptides that bind to GRP receptors. The peptides are Bombesin analogs wherein the first and optionally the third amino acid are modified.

15 Claims, No Drawings

OTHER PUBLICATIONS

M. E. Rosenfeld, et al., Adenoviral Mediated Delivery of Gastrin–releasing Peptide Receptor Results in Specific Tumor Localization of a Bombesin Analogue In Vivo, Clinical Cancer Research, vol. 3 (Jul. 1997), pp. 1187–1194, American Association for Cancer Research, U.S.A.

Hoffman, et al., Rh–105 Bombesin Analogs: Selective In Vivo Targeting of Prostrate Cancer with a Therapeutic Radionuclide, The Journal of Nuclear Medicine, vol. 39, (1998), p. No. 982, Society of Nuclear Medicine, U.S.A. (abstract No. 882).

Schibli, Hoffman, Volkert, et al., A Tc–99m DITHIA–DI (Bis–Hydroxymethylene) Phosphine Conjugate of Bombesin: In Vitro and In Vivo Studies, The Journal of Nuclear Medicine, vol. 39 (May 1998 Supplement), p. 225P, Society of Nuclear Medicine, U.S.A. abstract No. 987.

Hoffman, Sieckman & Volkert, Targeting Small Cell Lung Cancer Using Iodinated Peptide Analogs, The Journal of Labelled Compound and Radiopharmaceuticals, vol. 37, (1995), pp. 321–325, John Wiley & Sons, Inc., U.S.A.

Halmos, Wittliff and Schally, Characterization of Bombesin/ Gastrin–releasing Peptide Receptors in Human Breast Cancer and Their Relationship to Steroid Receptor Expression, Cancer Research, vol. 55, (Jan. 15, 1955) pp. 280–287, American Association of Cancer Research, U.S.A.

RADIOLABELED PEPTIDES FOR THE DIAGNOSIS AND TREATMENT OF BREAST AND PROSTATE TUMORS AND METASTASES OF SUCH TUMORS

APPLICATION CROSS-REFERENCE

This patent application is a continuation application of U.S. patent application Ser. No. 09/485,085 filed Feb. 3, 2000, currently abandoned, which claims priority to International Application No. PCT/US99/12414 filed Jun. 3, 1999, published in English, which claims priority to U.S. Provisional Patent Application Ser. No. 60/088,517 filed Jun. 8, 1998, now abandoned, and claims priority to U.S. Provisional Patent Application Ser. No. 60/088,074 field Jun. 5, 1998, now abandoned.

BACKGROUND OF THE INVENTION

The present invention relates compounds and methods for the diagnosis and treatment of breast and prostate tumors and metastases thereof, and more particularly to radiolabeled Bombesin peptide analogs for the diagnosis and treatment of breast and prostate tumors and metastases thereof.

Many tumors have biochemical receptors that cause certain molecules, typically peptides or proteins, to bind to the tumor. One approach to diagnose tumors is to identify a compound that binds to a particular tumor and radiolabel the compound with a suitable radionuclide. The labeled compound is then administered the patient, generally via intravenous injection, and allowed to bind to the tumor. The tumor is then located by imaging the location where the radioactive decay occurs. While this concept as presented appears rather simple, in practice it is quite difficult. The first challenge is to identify a candidate compound. If the compound does not bind very strongly to the tumor and for a sufficient period of time, it will not be possible to obtain adequate diagnosis. Further, even if the compound binds to the tumor, if it also binds to surrounding healthy tissue, the diagnosis will be difficult or impossible. Moreover, it is necessary that the linkage of the compound to the radionuclide not disturb the affinity of the tumor for the compound. Another issue is the potential toxicity of the compound in the patient. Compounds that may be very suitable from a binding perspective may be too toxic to use.

A similar approach can be taken in tumor therapy, where one would identify a suitable compound, radiolabel the compound and administer the compound to the patient. The compound is generally administered via intravenous injection, but may to administered by direct injection into the tumor mass. The radionuclide will then decay, releasing energy to kill or reduce the growth of the tumor. Again, the concept is simple, but in practice there are many difficulties. In addition to the problems mentioned above, it is necessary that there be very little of the compound anywhere in the body except in the tumor, due to the danger of the high-energy radiation to healthy tissue. This means that not only must the compound bind very strongly to the tumor, there must be little or no binding to healthy tissues, even if they are not in the vicinity of the tumor.

Attempts to locate suitable compounds have been fraught with difficulty. Because it is desirable to screen large numbers of potential compounds quickly, various "shortcut" assays and models have been developed. Unfortunately, many of these techniques have produced incorrect or misleading data.

Many researchers have used cell line cultures to screen compounds. While the use of cell lines as a screening technique has advantages, it has been found that cell line cultures often have binding affinity for compounds that is not exhibited by actual tumors. Thus the data from this technique produces false positives.

Other researchers have used homogenates of tumors, where a sample of the tumor has been subjected to high shear in a laboratory blender. One problem with this technique is that not only the tumor, but also surrounding tissues that were attached to the tumor are included in the homogenate, thus rendering it impossible to know if any binding affinity is from the tumor or from the surrounding tissues. Further, the shear of the homogenization breaks open the cell membranes, allowing for the possibility of binding that would not occur in an intact cell.

A screening method that produces unambiguous results is a morphological study in which sections (thin slices) of a tumor and surrounding tissue are contacted with a candidate compound that has been labeled with a radionuclide that is suitable for exposing photographic film. This technique clearly differentiates between receptors that are present in the tumor and those present in the surrounding tissue. Unfortunately, this technique is very labor intensive and depends on having suitable tumor tissue samples available.

Peptides and other compounds have been used without radiolabeling to affect the growth of tumors. While some of these compounds may be useful with radiolabeling for imaging and radiotherapy, the correlation between compounds useful for chemotherapy and those useful for radiotherapy is very low.

Bombesin is a peptide originally isolated from frog skin. It is an example of a compound that binds to GRP (Gastrin Releasing Peptide) receptors. Bombesin has the structure:

pGlu-Gln-Arg-Leu-Gly-Asn-Gln-Trp-Ala-Val-Gly-His-Leu-Met-$NH_2$ (SEQ ID NO: 1)

Considerable work has been conducted in an attempt to identify tumor and non-tumor GRP receptors. Unfortunately, much of that work has yielded results that are inaccurate or misleading.

Breeman et al. "[$^{111}$In-DTPA$^0$ Pro', Tyr$^4$] bombesin: Studies In Vitro and in Rats", *JNM* 39 (1998) 62P teach that high and specific uptake was found in the pancreas and tissues of the GI-tract. Uptake was blocked by iv co-injection of 100 ug of Tyr$^4$-BN with the radiolabeled peptide, but not when administered 1 hour after theradiotracer indicating the internalization of the radioligand.

Hoffman, Li, Sieckman, and Volkert, "Uptake and Retention of a Rh-105 Bombesin Analogue in GRP Receptor Expressing Neoplasms: An In Vitro Study", *JNM* 38 (1997) 188P–189P (abstract) teach that the affinity of a Rh-105 labeled bombesin analog for the GRP receptor was investigated along with its prolonged cellular retention in the PC-3 human prostate cancer cell line (65% @ 2 h) and CF-PAC1 human pancreatic cell line (41% @ 2 h). The Rh-105 analog was rapidly internalized intracellularly in both cell lines studied. The author states that the selective affinity & prolonged retention in neoplastic cells make this radiolabeled peptide a potential candidate for radiotherapy.

Hoffman, Li, Volkert, Sieckman, Higginbotham, and Ochrymowycz, "Synthesis and Characterization of Rh-105 Labelled Bombesin Analogues: Enhancement of GRP Binding Affinity Utilizing Aliphatic Carbon Chain Linkers", *Journal of Labelled Compound and Radiopharmaceuticals* 40 (1997) 490–492 (abstract) teach that the $IC_{50}$ values (using Swiss 3T3 fibroblasts) were determined for a series of 4 peptides and the non-metalated sulfur macrocyclic analogs expressed similar affinities to the GRP receptor than the parent BBN peptide. Upon Rh (III) complexation, decreasing the proximity of the Rh (III) $C_{12-16}$ and $S_4$ complex to the binding region of BBN, increases the affinity of the final metalated peptide for the GRP receptor. This data may have implications in preparing other metalated BBN analogues which maintain specificity and high affinity for GRP receptors expressed on neoplastic cells.

Hoffman, Sieckman, Ochrymowycz, Higginbotham, Volkert, and Ketring, "In Vitro and In Vivo Characterization of a Rh-105-Tetrathiamacrocycle Conjugate of a Labelled Bombesin Analogue", *JNM* 37 (1996) 61P teach that biodistribution studies of the Rh-105 analogue in normal mice showed predominant clearance into the urine and low retention in the kidneys. Data demonstrate the feasibility of forming Rh-105 conjugates with BBN analogs as potential therapeutic agents that specifically target neoplastic cells expressing BBN2 receptors.

Hoffman et al. "Rh-105 Bombesin Analogs: Selective In Vivo Targeting of Prostate Cancer with a Radionuclide" *JNM* 39 (1998) 982P teach that an Rh-105 BBN (7 14) analog, with a 4 carbon spacer between the sulfur macrocycle and the Q amino acid was evaluated in nude mice possessing PC-3 prostatic tumors. Tumor/Muscle ratios were 7.8, 7.7, and 13.6 @ 4, 24, & 48 hours p. i., respectively. The conclusion is that the selective affinity and prolonged retention of this radiolabeled peptide in prostatic cancer cells makes it an attractive candidate for radiotherapy.

T. J. Hoffman, G. L Sieckman, and W. A. Volkert, "Iodinated Bombesin Analogues: Effect of N-terminal vs. Side Chain Iodine Attachment on BBN-GRP Receptor Binding", *JNM* 37 (1996) 185P teaches that assessed iodinated BBN analogs as potential SCLC targeting vectors. In all cases, the specific binding region, BBN (8–13) or W-A-V-G-H-L (SEQ ID NO: 2), was maintained, as well as amidation of the carboxy terminal end. Measurement of $IC_{50}$ values were conducted utilizing Swiss 3T3 cells with $[^{125}I]$ $[Tyr^4]$ BBN. The loss of receptor affinity by the mIP-$Lys^7$ conjugated peptide suggests that incorporation of Lys between BBN (1–6) may facilitate increased peptide-receptor affinity. The data show that N-terminal iodination of these analogs may provide a viable route to obtain high affinity BBN iodinated peptides.

Schibli, Hoffman, Volkert. et al. "A Tc-99m DITHIA-DI (Bis-Hydroxymethylene) Phosphine conjugate of Bombesin In Vivo Studies *JNM* 39 (1998) 225P teaches that the Tc-99 analogs of bombesin derived from 2 different DADT BFCs and the 14 amino acid peptide Lys-3-bombesin were evaluated in a competitive binding assay vs. $[^{125}I]$ $[Tyr^4]$ bombesin using human prostate cancer PC-3 cell membranes. The results indicate that the Tc-99m complexes have the potential to be used in the characterization of bombesin/GRP receptors of prostate cancer non-invasively in vivo.

Baidoo et al. "Synthesis and Evaluation of High Affinity Technetium Bombesin Analogs", *JNM* 38 (1997) 87P mentions prostate, breast, gastric, colon, pancreatic and scl cancers. DADT chelates (1 and 2, resulting in neutral or positive cores) were attached to the lysine residue & commat; N-terminal region of the potent Bn analog Pyr-Q-K-L-Q-N-Q-W-A-V-G-H-L-M-$NH_2$ (SEQ ID NO: 3). When a DADT peptide was labeled with Tc-99m or Tc-99,2 isomers resulted. The Tc-99 analogs exhibited high affinity in a rat cortex membrane binding assay vs. $[^{125}I]$ $[Tyr^4]$ bombesin.

B. Rogers, D. Curiel, K. Laffoon, D. Buchsbaum, "Synthesis and Radiolabeling of Bombesin Derivatives with Copper-64 and Binding to Cells Expressing the Gastrin Releasing Peptide Receptor", *Journal of Labelled Compounds and Radiopharmaceuticals* 40 (1997) 482 (abstract) concludes that Cu-64-TETA-Aoc BBN (7–14) is a potential therapeutic radiopharmaceutical that can be used to treat GRPr positive tumors.

A. Safavy, M. Khazaeli, H. Qin, and D. Buchsbaum, "Synthesis of Bombesin Analogues for Radiolabeling Rhenium-188", *Cancer* 80 (1997) 2354–2359 teaches that 7-amino acid analogue of BBN was synthesized and conjugated to the hydroxamate ligand trisuccin. Radiolabeling with Re-188 were performed in >90% yield. Cell-binding performed with BNR-11 (3T3 mouse fibroblast cells) and PC-3 human prostate carcinoma GRPA positive cells resulted in positive binding.

B. Rogers et al. "Tumor Localization of a Radiolabeled Bombesin Analog in Mice Bearing Human Ovarian Tumors Induced to Express GRP Receptor by an Adenoviral Vector", *Cancer* 80 (1997) 2419–2424 shows a study was conducted to determine the level of localization of $[^{125}I/^{131}I]$-mIP-bombesin in tumors.

Rogers, Buchsbaum, et al. "Localization of I-125-mIP-Des-MetI4-bombesin (7–13) $NH_2$ in Ovarian Carcinoma Induced to Express the GRPr by Adenoviral Vector Mediated Gene Transfer", *JNM* 38 (1997) 1221–1229 teaches that $[^{125}I]$ $[Tyr^4]$ bombesin was compared to [1211]-mIP-bombesin (a 7 aa BN analog) for in vitro binding and internalization into tumor cells and for tumor localization in vivo, and results showed that the latter has more favorable characteristics with regards to tumor localization and cellular internalization & retention.

Zinn, Buchsbaum, et al. "Imaging Adenoviral-Mediated Gene Transfer of GRPr Using a Tc-99m-Labelled Bombesin Analogue". *JNM* 39 (1998) 224P-225P teaches that BBN analogue (QWAVGHLM; SEQ ID NO: 4) was HYNIC modified and radiolabeled with Tc-99m using tricine as a transchelator. Specific and high affinity binding to GRPr-expressing cells was demonstrated by Scatchard analysis. Favorable biodistribution and imaging were observed.

M. E. Rosenfeld et al. Adenoviral Mediated Delivery of GRPr Results in Specific Tumor Localization of a Bombesin Analogue In Vivo", *Clin. Cancer Res.* 3 (1997), 1187–1194 teaches similar work to previous publication above.

T. J. Hoffman, G. L. Sieckman and W. A. Volkert. "Targeting Small Cell Lung Cancer Using Iodinated Peptide Analogs" teaches that 5 analogs prepared using SPPS and in vitro BB2 receptor binding assessed using Swiss T3T fibroblasts. Amino acids #1–6 nor C-terminal Met residue are not essential to maintain receptor specificity. Results imply that incorporation of I-123 or I-131 as a m-iodophenyl moiety may be used to diagnose or treat sclc.

U.S. Pat. No. 5,686,410 Novartis Albert teaches radiolabeled bombesin and antagonists, including use for tumor imaging and therapy (Examples 11 and 12).

There are numerous articles and patents that discuss the binding of non-radioactive bombesin analogs to various tissues such as SCLC (small cell lung cancer), and pituitary, adrenal, and skin tumors.

SUMMARY OF THE INVENTION

An aspect of the present invention is to provide pharmaceutical composition for targeting a selected biological site, the composition comprising:

a peptide $AA_1$-Gln-$AA_3$-Leu-Gly-Asn-Gln-Trp-Ala-Val-Gly-His-Leu-Met-NH2 (SEQ ID NO: 5)

wherein AA₁ is a cyclic amino acid of the formula wherein n=0 to 5;
wherein AA₃ is selected from the group consisting of Arg, wherein n'=0 to 2, and wherein n=1 to 3 and n'=0 to 3.

Another aspect of the present invention is to provide methods for the diagnosis and treatment of tumors utilizing the peptides of the present invention.

These are merely two illustrative aspects of the present invention and should not be deemed an all-inclusive listing of the innumerable aspects associated with the present invention. These and other aspects will become apparent to those skilled in the art in light of the following disclosure.

DETAILED DESCRIPTION OF THE INVENTION

In this specification and claims, numerical values and ranges are not critical unless otherwise stated. The numerical values and ranges herein may be read as if they were prefaced with the words "about" or "substantially".

The invention provides peptides that are analogs of bombesin. By "analogs of bombesin" is meant any compound that binds to a GRP receptor. GRP receptors are overexpressed in prostate cancer, breast cancer, and metastases thereof. A particularly preferred analog of bombesin has the formula:

pGlu-Gln-Arg-Tyr-Gly-Asn-Gln-Trp-Ala-Val-Gly-His-Leu-Met-NH₂ (SEQ ID NO: 6). This compound is also known as Tyr⁴-bombesin.

The peptides of the present invention include novel isosteric modifications at the N-terminal of bombesin to enable the introduction of chelating groups. Modification at the third position of the bombesin molecules is also introduced. This results in the retention of agonist and internalization properties of the molecules. Radiolabeling of these molecules with imaging and therapeutic isotopes has applications in the detection and treatment of GRP and Bombesin receptor positive tumors.

Three classes of bombesin analogs have been developed. The first class of peptide involves replacement of p-Glu. The p-Glu at the N-terminal of the peptide chain does not lend itself to the attachment of chelating moieties either by conventional means or by solid phase methods. It has been determined that the p-Glu moiety can be replaced with cyclic amino acids without loss of binding characteristics. Replacement moieties include specifically Proline (Pro) and other cyclic analogs that provide the same tertiary structures the N-terminal. Such a replacement provides a reactive moiety for the attachment of polyamino carboxylate chelating groups, $N_tS_{4-t}$ chelating agents and other chelating agents.

Such an isosteric replacement of pGlu by Pro preserves the binding characteristics of the peptide. Other replacements include pipecolic acid and its homologs and isomers, and cyclic compounds of the formula below containing at least one reactive amine to which the chelating agent may attach.

wherein n=0 to 5;
(n=0 is Proline, n=1 is Pip (pipecolic acid) and isomers).

Suitable cyclic compounds include Pro, Pip, hPip (homopipecolic acid), Moc (morpholino 2-carboxylic acid) and Mtc (thiomorpholino 2-carboxylic acid).

Other cyclic compounds for the replacement of pGlu include the presence of a heteroatom in place of one of the carbons in the ring above. Suitable heteroatoms include O, S and N—R, wherein R=$C_1$ to $C_6$ normal or branched.

In addition, the —CO— group can be replaced by an alkyl spacer wherein n=0 to 10, and a reactive group selected from the group consisting of COOH, NCS (isothiocyanate), NCO (isocyanate), and carbomoyl group (OCOX where X is a reactive moiety such as halogen or other reactive moiety). These reactive groups can also be separated from the cyclic moiety by spacer groups of branched or normal alkyl chains with or without intervening heteroatoms.

The reactive groups for the attachment to the peptide chain indicated can be located at any position of the ring and can be separated by a spacer.

If the attachment of the reactive group is located adjacent to the N-atom containing the chelating moiety or the heteroatom, the attachment can either have either L or D-configuration.

In the above peptides, suitable chelating agents include DTPA, DTPA', DOTA, $N_tS_{4-t'}$.

The second class of bombesin analogs involves replacing the third amino acid of the sequence, Arg, by a chemical equivalent. Such chemical equivalents include, but are not limited to the following:

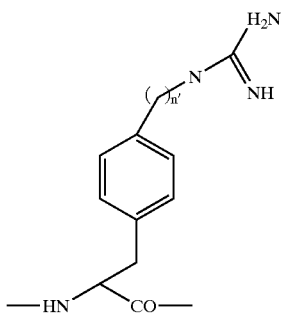

wherein n'=0–2 (p-gPhe (n'=0), p-gmPhe (n'=1), p-gePhe (n'=2) and

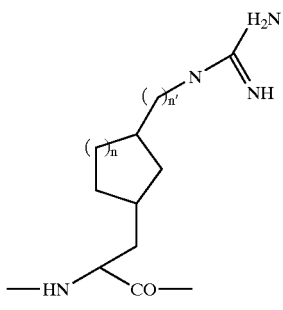

wherein n=1 to 3 and n"=0 to 3.

n=1–3 and n'=0–3 g-Cpa (n=1, n'=0), gm-Cpa (n=1, n'=1), ge-Cpa (n=1, n'=2), gp-Cpa (n=1, 3)n'=g-Cha (n=2. n'=0), gm-Cha (n=2, n'=1), ge-Gha (n=2, n'=2), gp-Cha (n=2, 3)n'=g-Chpa (n=2, n'=0), gm-Chpa (n=2, n'=1) ge-Chpa (n=2, n'=2), gp-Chpa (n n'=3),=2.

The third class of peptide of the present invention involves replacing the pGlu of bombesin by L or D-His-$AA_1$, or L-His-b-Asp-$AA_1$, or D-His-Asp-$AA_1$. (Note: $AA_1$, is same as in part a, above). Examples of this class of peptide include:

L-(D)-His-AA1Gln-AA3-AA4Gly-Asn-Gln-Trp-Ala-Val-Gly-His-Leu-AA14-$NH_2$L-(SEQ ID) NO: 7) (D)-His-b-Asp-AA1-Gln-AA3-AA4-Gly-Asn-Gln-Trp-Ala-Val-Gly-His-Leu AA14-$NH_2$ (SEQ ID NO: 8).

Synthesis of the peptides of the present invention may be accomplished by any suitable technique. These techniques generally involve successive condensations of protected amino acids and are well known in the art.

Examples of suitable peptides of the present invention include the following compounds. The compounds are shown with DTPA as the chelating agent for purposes of illustration only. DTPA can be replaced with any suitable chelating agent.

```
DTPA-pGlu-Gln-Arg-Tyr-Gly-Asn-Gln-Trp-Ala-Val-Gly-His-Leu-Met-NH2      (SEQ ID NO:9)
DTPA-Pro-Gln-Arg-Tyr-Gly-Asn-Gln-Trp-Ala-Val-Gly-His-Leu-Met-NH2       (SEQ ID NO:10)
DPTA-Pip-Gln-Arg-Tyr-Gly-Asn-Gln-Trp-Ala-Val-Gly-His-Leu-Met-NH2       (SEQ ID NO:11)
DTPA-hPip-Gln-Arg-Tyr-Gly-Asn-Gln-Trp-Ala-Val-Gly-His-Leu-Met-NH2      (SEQ ID NO:12)
DTPA-Pro-Gln-Arg-Tyr-Gly-Asn-Gln-Trp-Ala-Val-Gly-His-Leu-Nle-NH2       (SEQ ID NO:13)
DTPA-Pip-Gln-Arg-Tyr-Gly-Asn-Gln-Trp-Ala-Val-Gly-His-Leu-Nle-NH2       (SEQ ID NO:14)
DTPA-hPip-Gln-Arg-Tyr-Gly-Asn-Gln-Trp-Ala-Val-Gly-His-Leu-Nle-NH2      (SEQ ID NO:15)
DTPA-Moc-Gln-Arg-Tyr-Gly-Asn-Gln-Trp-Ala-Val-Gly-His-Leu-Met-NH2       (SEQ ID NO:16)
DTPA-Mtc-Gln-Arg-Tyr-Gly-Asn-Gln-Trp-Ala-Val-Gly-His-Leu-Met-NH2       (SEQ ID NO:17)
DTPA-Pro-Gln-gPhe-Tyr-Gly-Asn-Gln-Trp-Ala-Val-Gly-His-Leu-Met-NH2      (SEQ ID NO:18)
DTPA-Pro-Gln-gmPhe-Tyr-Gly-Asn-Gln-Trp-Ala-Val-Gly-His-Leu-Met-NH2     (SEQ ID NO:19)
DTPA-Pro-Gln-gePhe-Tyr-Gly-Asn-Gln-Trp-Ala-Val-Gly-His-Leu-Met-NH2     (SEQ ID NO:20)
DTPA-Pip-Gln-gPhe-Tyr-Gly-Asn-Gln-Trp-Ala-Val-Gly-His-Leu-Met-NH2      (SEQ ID NO:21)
DTPA-Pip-Gln-gmPhe-Tyr-Gly-Asn-Gln-Trp-Ala-Val-Gly-His-Leu-Met-NH2     (SEQ ID NO:22)
DPTA-Pip-Gln-gePhe-Tyr-Gly-Asn-Gln-Trp-Ala-Val-Gly-His-Leu-Met-NH2     (SEQ ID NO:23)
DPTA-hPip-Gln-gPhe-Tyr-Gly-Asn-Gln-Trp-Ala-Val-Gly-His-Leu-Met-NH2     (SEQ ID NO:24)
DTPA-Moc-Gln-gmPhe-Tyr-Gly-Asn-Gln-TrP-Ala-Val-Gly-His-Leu-Met-NH2     (SEQ ID NO:25)
DPTA-Mtc-Gln-gePhe-Tyr-Gly-Asn-Gln-Trp-Ala-Val-Gly-His-Leu-Met-NH2     (SEQ ID NO:26)
DTPA-Pro-Gln-gCpa-Tyr-Gly-Asn-Gln-Trp-Ala-Val-Gly-His-Leu-Met-NH2      (SEQ ID NO:27)
DPTA-Pro-Gln-gmCpa-Try-Gly-Asn-Gln-Trp-Ala-Val-Gly-His-Leu-Met-NH2     (SEQ ID NO:28)
DPTA-Pro-Gln-geCpa-Tyr-Gly-Asn-Gln-Trp-Ala-Val-Gly-His-Leu-Met-NH2     (SEQ ID NO:29)
```

-continued

| | |
|---|---|
| DPTA-Pro-Gln-gpCpa-Tyr-Gly-Asn-Gln-Trp-Ala-Val-Gly-His-Leu-Met-NH$_2$ | (SEQ ID NO:30) |
| DPTA-Pro-Gln-gCha-Tyr-Gly-Asn-Gln-Trp-Ala-Val-Gly-His-Leu-Met-NH$_2$ | (SEQ ID NO:31) |
| DPTA-Pro-Gln-gmCha-Tyr-Gly-Asn-Gln-Trp-Ala-Val-Gly-His-Leu-Met-NH$_2$ | (SEQ ID NO:32) |
| DPTA-Pro-Gln-geCha-Tyr-Gly-Asn-Gln-Trp-Ala-Val-Gly-His-Leu-Met-NH$_2$ | (SEQ ID NO:33) |
| DPTA-Pro-Gln-gpCha-Tyr-Gly-Asn-Gln-Trp-Ala-Val-Gly-His-Leu-Met-NH$_2$ | (SEQ ID NO:34) |
| DPTA-Pro-Gln-gChpa-Tyr-Gly-Asn-Gln-Trp-Ala-Val-Gly-His-Leu-Met-NH$_2$ | (SEQ ID NO:35) |
| DPTA-Pro-Gln-gmChpa-Tyr-Gly-Asn-Gln-Trp-Ala-Val-Gly-His-Leu-Met-NH$_2$ | (SEQ ID NO:36) |
| DPTA-Pro-Gln-geChpa-Tyr-Gly-Asn-Gln-Trp-Ala-Val-Gly-His-Leu-Met-NH$_2$ | (SEQ ID NO:37) |
| DPTA-Pro-Gln-gpChpa-Tyr-Gly-Asn-Gln-Trp-Ala-Val-Gly-His-Leu-Met-NH$_2$ | (SEQ ID NO:38) |
| DTPA-Pip-Gln-gCpa-Tyr-Gly-Asn-Gln-Trp-Ala-Val-Gly-His-Leu-Met-NH$_2$ | (SEQ ID NO:39) |
| DTPA-Pip-Gln-gmCpa-Tyr-Gly-Asn-Gln-Trp-Ala-Val-Gly-His-Leu-Met-NH$_2$ | (SEQ ID NO:40) |
| DTPA-Pip-Gln-geCpa-Tyr-Gly-Asn-Gln-Trp-Ala-Val-Gly-His-Leu-Met-NH$_2$ | (SEQ ID NO:41) |
| DPTA-Pip-Gln-gpCpa-Tyr-Gly-Asn-Gln-Trp-Ala-Val-Gly-His-Leu-Met-NH$_2$ | (SEQ ID NO:42) |
| DPTA-Pip-Gln-gCha-Tyr-Gly-Asn-Gln-Trp-Ala-Val-Gly-His-Leu-Met-NH$_2$ | (SEQ ID NO:43) |
| DPTA-Pip-Gln-gmCha-Tyr-Gly-Asn-Gln-Trp-Ala-Val-Gly-His-Leu-Met-NH$_2$ | (SEQ ID NO:44) |
| DPTA-Pip-Gln-geCha-Tyr-Gly-Asn-Gln-Trp-Ala-Val-Gly-His-Leu-Met-NH$_2$ | (SEQ ID NO:45) |
| DPTA-Pip-Gln-gpCha-Tyr-Gly-Asn-Gln-Trp-Ala-Val-Gly-His-Leu-Met-NH$_2$ | (SEQ ID NO:46) |
| DTPA-Pip-Gln-gChPa-Tyr-Gly-Asn-Gln-Trp-Ala-Val-Gly-His-Leu-Met-NH$_2$ | (SEQ ID NO:47) |
| DPTA-Pip-Gln-gmChpa-Tyr-Gly-Asn-Gln-Trp-Ala-Val-Gly-His-Leu-Met-NH$_2$ | (SEQ ID NO:48) |
| DPTA-Pip-Gln-geChpa-Tyr-Gly-Asn-Gln-Trp-Ala-Val-Gly-His-Leu-Met-NH$_2$ | (SEQ ID NO:49) |
| DPTA-Pip-Gln-gpChpa-Tyr-Gly-Asn-Gln-Trp-Ala-Val-Gly-His-Leu-Met-NH$_2$ | (SEQ ID NO:50) |
| DPTA-hPip-Gln-gCpa-Tyr-Gly-Asn-Gln-Trp-Ala-Val-Gly-His-Leu-Met-NH$_2$ | (SEQ ID NO:51) |
| DPTA-hPip-Gln-gmCpa-Tyr-Gly-Asn-Gln-Trp-Ala-Val-Gly-His-Leu-Met-NH$_2$ | (SEQ ID NO:52) |
| DPTA-hPip-Gln-geCpa-Tyr-Gly-Asn-Gln-Trp-Ala-Val-Gly-His-Leu-Met-NH$_2$ | (SEQ ID NO:53) |
| DPTA-hPip-Gln-gpCpa-Tyr-Gly-Asn-Gln-Trp-Ala-Val-Gly-His-Leu-Met-NH$_2$ | (SEQ ID NO:54) |
| DPTA-hPip-Gln-gCha-Tyr-Gly-Asn-Gln-Trp-Ala-Val-Gly-His-Leu-Met-NH$_2$ | (SEQ ID NO:55) |
| DPTA-hPip-Gln-gmCha-Tyr-Gly-Asn-Gln-Trp-Ala-Val-Gly-His-Leu-Met-NH$_2$ | (SEQ ID NO:56) |
| DPTA-hPip-Gln-geCha-Tyr-Gly-Asn-Gln-Trp-Ala-Val-Gly-His-Leu-Met-NH$_2$ | (SEQ ID NO:57) |
| DPTA-hPip-Gln-gpCha-Tyr-Gly-Asn-Gln-Trp-Ala-Val-Gly-His-Leu-Met-NH$_2$ | (SEQ ID NO:58) |
| DPTA-hPip-Gln-gChpa-Tyr-Gly-Asn-Gln-Trp-Ala-Val-Gly-His-Leu-Met-NH$_2$ | (SEQ ID NO:59) |
| DPTA-hPip-Gln-gmChpa-Tyr-Gly-Asn-Gln-Trp-Ala-Val-Gly-His-Leu-Met-NH$_2$ | (SEQ ID NO:60) |
| DPTA-hPip-Gln-geChpa-Tyr-Gly-Asn-Gln-Trp-Ala-Val-Gly-His-Leu-Met-NH$_2$ | (SEQ ID NO:61) |
| DPTA-hPip-Gln-gpChpa-Tyr-Gly-Asn-Gln-Trp-Ala-Val-Gly-His-Leu-Met-NH$_2$ | (SEQ ID NO:62) |
| DPTA-Moc-Gln-gCpa-Tyr-Gly-Asn-Gln-Trp-Ala-Val-Gly-His-Leu-Met-NH$_2$ | (SEQ ID NO:63) |
| DPTA-Moc-Gln-gmCpa-Tyr-Gly-Asn-Gln-Trp-Ala-Val-Gly-His-Leu-Met-NH$_2$ | (SEQ ID NO:64) |
| DPTA-Moc-Gln-geCpa-Tyr-Gly-Asn-Gln-Trp-Ala-Val-Gly-His-Leu-Met-NH$_2$ | (SEQ ID NO:65) |
| DPTA-Moc-Gln-gpCpa-Tyr-Gly-Asn-Gln-Trp-Ala-Val-Gly-His-Leu-Met-NH$_2$ | (SEQ ID NO:66) |
| DPTA-Moc-Gln-gCha-Tyr-Gly-Asn-Gln-Trp-Ala-Val-Gly-His-Leu-Met-NH$_2$ | (SEQ ID NO:67) |

-continued

```
DPTA-Moc-Gln-gmCha-Tyr-Gly-Asn-Gln-Trp-Ala-Val-Gly-His-Leu-Met-NH2        (SEQ ID NO:68)

DPTA-Moc-Gln-geCha-Tyr-Gly-Asn-Gln-Trp-Ala-Val-Gly-His-Leu-Met-NH2        (SEQ ID NO:69)

DPTA-Moc-Gln-gpCha-Tyr-Gly-Asn-Gln-Trp-Ala-Val-Gly-His-Leu-Met-NH2        (SEQ ID NO:70)

DPTA-Moc-Gln-gChpa-Tyr-Gly-Asn-Gln-Trp-Ala-Val-Gly-His-Leu-Met-NH2        (SEQ ID NO:71)

DPTA-Moc-Gln-gmChpa-Tyr-Gly-Asn-Gln-Trp-Ala-Val-Gly-His-Leu-Met-NH2       (SEQ ID NO:72)

DPTA-Moc-Gln-geChpa-Tyr-Gly-Asn-Gln-Trp-Ala-Val-Gly-His-Leu-Met-NH2       (SEQ ID NO:73)

DPTA-Moc-Gln-gpChpa-Tyr-Gly-Asn-Gln-Trp-Ala-Val-Gly-His-Leu-Met-NH2       (SEQ ID NO:74)

DPTA-Mtc-Gln-gCpa-Tyr-Gly-Asn-Gln-Trp-Ala-Val-Gly-His-Leu-Met-NH2         (SEQ ID NO:75)

DPTA-Mtc-Gln-gmCpa-Tyr-Gly-Asn-Gln-Trp-Ala-Val-Gly-His-Leu-Met-NH2        (SEQ ID NO:76)

DPTA-Mtc-Gln-geCpa-Tyr-Gly-Asn-Gln-Trp-Ala-Val-Gly-His-Leu-Met-NH2        (SEQ ID NO:77)

DPTA-Mtc-Gln-gpCpa-Tyr-Gly-Asn-Gln-Trp-Ala-Val-Gly-His-Leu-Met-NH2        (SEQ ID NO:78)

DPTA-Mtc-Gln-gCha-Tyr-Gly-Asn-Gln-Trp-Ala-Val-Gly-His-Leu-Met-NH2         (SEQ ID NO:79)

DPTA-Mtc-Gln-gmCha-Tyr-Gly-Asn-Gln-Trp-Ala-Val-Gly-His-Leu-Met-NH2        (SEQ ID NO:80)

DPTA-Mtc-Gln-geCha-Tyr-Gly-Asn-Gln-Trp-Ala-Val-Gly-His-Leu-Met-NH2        (SEQ ID NO:81)

DPTA-Mtc-Gln-gpCha-Tyr-Gly-Asn-Gln-Trp-Ala-Val-Gly-His-Leu-Met-NH2        (SEQ ID NO:82)

DPTA-Mtc-Gln-gChpa-Tyr-Gly-Asn-Gln-Trp-Ala-Val-Gly-His-Leu-Met-NH2        (SEQ ID NO:83)

DPTA-Moc-Gln-gmChpa-Tyr-Gly-Asn-Gln-Trp-Ala-Val-Gly-His-Leu-Met-NH2       (SEQ ID NO:84)

DPTA-Moc-Gln-geChpa-Tyr-Gly-Asn-Gln-Trp-Ala-Val-Gly-His-Leu-Met-NH2       (SEQ ID NO:85)

DPTA-Moc-Gln-gpChpa-Try-Gly-Asn-Gln-Trp-Ala-Val-Gly-His-Leu-Met-NH2       (SEQ ID NO:86)
```

The peptides of the present invention are bound to a suitable radionuclide. For diagnostic uses, suitable radionuclides include but are not limited to $^{133m}$In, $^{99m}$Tc, $^{67}$Ga, $^{52}$Fe, $^{68}$Ga, $^{72}$As, $^{111}$In, $^{97}$Ru, $^{203}$Pb, $^{62}$Cu, $^{64}$Cu, $^{51}$Cr, $^{52m}$Mn, $^{157}$Gd, $^{123}$I, $^{124}$I, $^{131}$I, $^{75}$Br, $^{76}$Br, $^{77}$Br, and $^{82}$Br with $^{99m}$Tc, $^{67}$Ga, $^{111}$In, and $^{123}$I being preferred.

For therapeutic uses, suitable radionuclides include but are not limited to $^{186}$Re, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{188}$Rd, $^{77}$As, $^{166}$Dy, $^{166}$Ho, $^{149}$Pm, $^{151}$Pm, $^{153}$Sm, $^{159}$Gd, $^{172}$Tm, $^{169}$Yb, $^{175}$Yb, $^{177}$Lu, $^{105}$Rh, $^{111}$Ag, $^{131}$I, $^{129}$I and $^{177m}$Sn with $^{186}$Re, $^{188}$Re, $^{90}$Y, $^{153}$Sm, $^{177}$Lu, and $^{131}$I being preferred.

The radionuclide and the peptide must be bound together. If the radionuclide is a radioactive halogen, the radioactive halogen may be bound directly to the peptide, such as by chemical reaction to a Tyr or Trp moiety of the peptide.

If the radionuclide is a radioactive metal, the radioactive metal may be bound to the peptide by means of a chelating agent. A chelating group may be attached to the peptide by an amide bond or through a spacing group, as is known in the art.

Suitable chelating groups for chelating said metal atoms are $N_tS_{(4-t)}$ tetradentate chelating agents, wherein t=2–4, or groups derived from ethylene diamine tetra-acetic acid (EDTA), diethylene triamine penta-acetic acid (DTPA), cyclohexyl 1,2-diamine tetra-acetic acid (CDTA), ethyleneglycol-0,0'-bis (2-aminoethyl)-N, N, N', N'-tetra acetic acid (EGTA), N, N-bis (hydroxybenzyl)-ethylenediamine-N, N'-diacetic acid (HBED), triethylene tetramine hexa-acetic acid (TTHA), 1,4,7,10 tetraazacyclododecane-N, N', N'', N'''-tetra-acetic acid (DOTA), hydroxyethyldiamine triacetic acid (HEDTA), 1,4,8,11-tetra-azacyclotetradecane-N, N', N'', N'''-tetra-acetic acid (TETA), substituted DTPA, substituted EDTA, or from a compound of the general formula

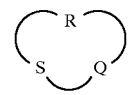

(I)

wherein R is a branched or non-branched, optionally substituted hydrocarbyl radical, which may be interrupted by one or more hetero-atoms selected from N, O and S and/or by one or more NH groups, and Q is a group which is capable of reacting with an amino group of the peptide and which is preferably selected from the group consisting of carbonyl, carbimidoyl, N—($C_1$–$C_6$) alkylcarbimidoyl, Nhydroxycarbimidoyl and N—($C_1$–$C_6$) alkoxycarbimidoyl.

$N_tS_{(4-t)}$ chelating agents, wherein t=2–4, are preferably selected from (II) 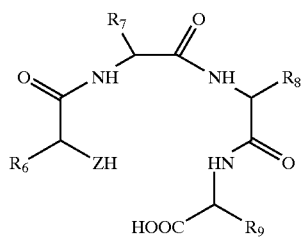

(III) 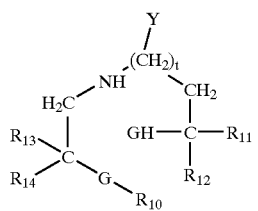

(IV) 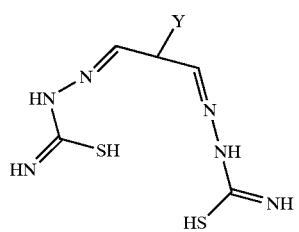

(V) 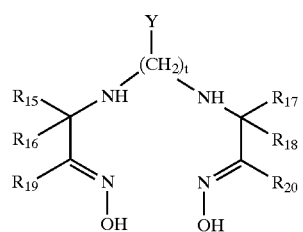

(VI) 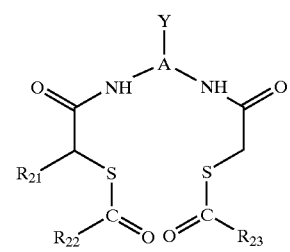

(VII) 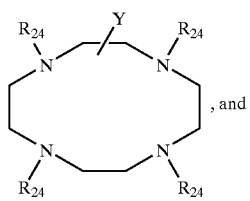

(VIII) 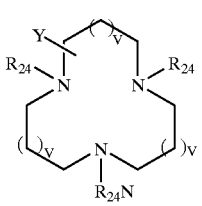

wherein:

$R_6$–$R_{20}$ are each individually hydrogen atoms or ($C_1$–$C_4$) alkyl groups, with the proviso that at least one of $C_6$ to $C_9$ is the symbol Y;

$R_{21}$ is a hydrogen atom or a $CO_2$ ($C_1$–$C_4$)alkyl group;

$R_{22}$ and $R_{23}$ are each individually ($C_1$–$C_4$) alkyl groups or phenyl groups;

v is 0 or 1;

t is 2 or 3;

$R_{24}$ is $CH_2$ COOH or a functional derivative thereof;

A is ($C_1$–$C_4$)alkylene, if desired substituted with $CO_2$alkyl, $CH_2CO$alkyl, $CONH_2$, $CONHCH_2CO_2$alkyl; phenylene, phenylene substituted by $CO_2$alkyl, wherein the alkyl groups have 1 to 4 carbon atoms;

G is NH or S;

Y is a functional group capable of binding with a free amino group of the peptide or with the spacing group; and Z is S or O.

Said functional group Y preferably comprises isocyanato, isothiocyanato, formyl, ohalonitrophenyl, diazonium, epoxy, trichloro-s-triazinyl, ethyleneimino, chlorosulfonyl, alkoxycarb-imidoyl, (substituted or unsubstituted) alkylcarbonyloxycarbonyl, alkylcarbonylimidazolyl, succinimido-oxycarbonyl; said group being attached to a ($C_1$–$C_{10}$) hydrocarbon biradical. Suitable examples of hydrocarbon biradicals are biradicals derived from benzene, ($C_1$–$C_6$) alkanes, ($C_2$–$C_6$) alkenes and ($C_1$–$C_4$)-alkylbenzenes.

Examples of suitable chelators of the general formula II are described in the international patent application WO 89/07456, such as unsubstituted or substituted 2imino-thiolanes and 2-imino-thiacyclohexanes, and in particular 2-imino-4mercaptomethylthiolane.

Suitable examples of spacing groups, if present in the metal-labelled peptide molecule, are groups of the general formula:

(IX) 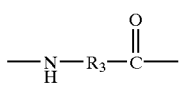

or (X) 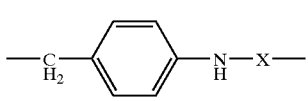

wherein $R_3$ is a $C_1$–$C_{10}$ alkylene group, a $C_1$–$C_{10}$ alkylidene group or a $C_2$–$C_{10}$ alkenylene group, and X is a thiocarbonyl group or a group of the general formula:

(XI) 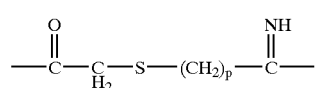

wherein p is 1–5.

Conjugates with avidin or biotin are formed as described by Paganelli et al. (*Int. J. Cancer* Kalofonos et al. (*J. Nucl. Med.* 1990, 31, 1791) and Anderson et al. (*FEBS LETT.* 1991, 282/1, 35–40).

The labeled peptides may be combined with carrier materials such as saline, and adjuvants, such as acids or bases added to alter the pH and/or act as buffers and/or preservatives. The use of carriers and adjuvants is well known to those skilled in the art.

The invention may be provided to the user by providing a suitable radiolabeled peptide of the invention in a carrier, with or without adjuvants, or by providing some or all of the necessary components in a kit. The use of a kit is particularly convenient since some of the components have a limited shelf life, particularly when combined. A suitable kit may include one or more of the following components (i) a peptide, (ii) a chelating agent, (iii) a carrier solution, (iv) a radioisotope, (v) a reducing agent, and (vi) instructions for their combination. Depending on the form of the radionuclide, a reducing agent may be a necessary to prepare the radionuclide for reaction with the peptide. Suitable reducing agents include Ce (III), Fe (II), Cu (I), Ti (III), Sb (III), and Sn (II). Of these, Sn (II) is particularly preferred.

For reasons of stability, it is generally preferred that the peptide be in a dry, lyophilized condition. The user adds the carrier solution to the dry peptide to reconstitute it. If it is desired to provide the peptide in solution form, it may be necessary to store it at lower temperatures than the dry form.

As mentioned above, the peptide and the chelating agent may be included separately in the kit. Alternatively, the peptide may be combined with the chelating agent prior to assembly of the kit.

Because of the short half-life of suitable radionuclides, it will frequently be most convenient to provide the kit to the user without the radionuclide. The radionuclide is then ordered separately when needed for a procedure. If the radionuclide is included in the kit, the kit will most likely be shipped to the user just before it is needed.

For diagnosis of tumors, the radiolabeled compounds are administered in an amount effective to allow tumor imaging. The quantitative amount will vary depending on the uptake of the compound by the tumor, the radioisotope chosen, and the sensitivity of the detection device (e.g.: gamma camera). Too little compound will not allow a sufficient radiation to permit diagnosis. Too much compound will cause large concentrations of the compound in the blood or nontargeted organs, and may also present unnecessary risk of toxicity to the patient. The selection of the effective amount is within the skill of one skilled in the art.

For treatment of tumors, the radiolabeled compounds are administered in a therapeutically effective amount. By "therapeutically effective amount" is meant an amount that will at least inhibit the growth or spread of the tumor, and preferably will cause the tumor to shrink or be completely eliminated. The quantitative amount will vary depending on the uptake of the compound by the tumor and the radioisotope chosen. Too little compound will not have sufficient effect. Too much compound will present unnecessary radiation exposure and risk of toxicity to the patient. The selection of the effective amount is within the skill a typical radiation oncologist.

Example 1

The peptide:
pGlu-Gln-Arg-Tyr-Gly-Asn-Gln-Trp-Ala-Val-Gly-His-Leu-Met-$NH_2$ (SEQ ID NO: 6)

([Tyr$^4$] bombesin) was synthesized using conventional solid phase techniques. It was labeled with $^{125}$I by the chloramine T iodination procedure, according to Greenwood, et al., *Biochemical Journal* 1963, 89, 114–123. The resulting compound:
pGlu-Gln-Arg-Tyr-Gly-Asn-Gln-Trp-Ala-Val-Gly-His-Leu-Met-$NH_2$ ([$^{125}$I-Tyr$^4$] SEQ ID NO: 87) bombesin, the "radioligand") was purified by HPLC, and had a specific activity of 1,000 Ci/mmol.

Example 2

Various tumor tissue samples, including surrounding tissue, were harvested from human patients and/or human cadavers, and frozen. The samples were cut on a cryostat, mounted on microscope slides, and then stored at −20° C. for at least 3 days to at least 3 days to improve adhesion of the tissue to the slide. The slide-mounted tissue sections were allowed to reach room temperature and preincubated in 50 mmol/l Tris-HCl, 130 mmol/l NaCl, 4.7 mmol/l KCl, 5 mmol/I $MgCl_2$, 1 mmol/l ethylene glycol-bi (b-aminoethylether)-N, N, N', N'-tetraacetic acid, and 0.5% bovine serum albumin, pH 7.4 (preincubation solution), for 30 min. at 25° C. The slides are then incubated in a solution containing the same medium as the preincubation solution except the bovine serum albumin is omitted, and the following compounds are added: 20000 dpm/100 ml of the radioligand of Example 1, 0.025% bacitracin, 1 mmol/l dithiothreitol, 2 mg/ml chymostatin, and 4 mg/ml leupeptin, pH=6.5. The slides are incubated at room temperature with the radioligand for 150 min., as described by Mantyh et al. (*Gasteroenterology*, 1994, 107, 1019–30). After the incubation, the slides are rinsed with four washes of 30 sec each in ice-cold preincubation solution, pH 7.4, dipped in ice-cold water, and then quickly dried in a refrigerator under a stream of cold air. The sections are subsequently exposed to a $^3$H Ultrofilm for 1 week, to detect the precise location of the radioactivity.

The films were evaluated to determine the ability to distinguish the tumor from the surrounding tissue. The results are shown in Table 1.

TABLE 1

| Tissue | Number of Samples | Number Positive | % Positive |
| --- | --- | --- | --- |
| Colon Cancer | 18 | 1 | 6 |
| Gastric Cancer | 27 | 0 | 0 |
| Pancreatic Cancer | 28 | 0 | 0 |
| Non Small Cell Lung Carcinoma | 34 | 0 | 0 |
| Small Cell Lung Carcinoma | 10 | 2 | 20 |
| Gastrinomas | 4 | 4 | 100 |
| Melanomas | 8 | 1 | 12 |
| Glioblastomas | 4 | 4 | 100 |
| Prostate Cancer | 28 | 28 | 100 |
| Prostate Cancer Metastases | 5 | 5 | 100 |
| Breast Cancer | 95 | 66 | 69 |
| Breat Cancer Metastases | 5 | 5 | 100 |
| Uterus Leomyosarcoma Tumor | 3 | 1 | 33 |

In Table 1, a tumor is considered "positive" if (1) a traditional histilogical examination of the tissue verifies that the tumor is present, (2) the film shows a clear image of the tumor, distinguishing it from the surrounding tissue, and (3) the film does not show an image of the tumor, if the tissue is first blocked with a nonradiolabeled sample of the peptide.

The data show that (1) gastrinomas, glioblastomas, prostate cancer, prostate cancer metastases, breast cancer, and breast cancer metastases show a high incidence of bombesin receptors (in the case of gastrinomas, prostate cancer, prostate cancer metastases, and breast cancer metastases, 100%);

and (2) a number of human tumors that were claimed by the literature to be bombesin receptor positive show no or very little positive results.

The negative data in Table 1 is important in understanding the instant invention. It has been widely reported (see, for example, Moody et al., *Peptides*, 683–686 (1993)), that small cell lung cancer has bombesin receptors. However, the data in Table 1 shows that only 20% of such tumors could be detected. Because of the highly specific nature of the method used to produce the data in Table 1, the data suggests that the techniques used in the prior art had fundamental defects.

Example 3

The peptide:

DTPA-Pro-Gln-Arg-Tyr-Gly-Asn-Gln-Trp-Ala-Val-Gly-His-Leu-Met-NH$_2$ (SEQ ID NO: 10)

[DTPA$^0$-Pro$^1$, Tyr$^4$] bombesin) was synthesized using conventional solid phase techniques. DTPA was introduced during the solid phase synthesis using tri-t-butyl DTPA. $^{111}$In labeling was performed according to the procedure described by W. H. Bakker, et al., *Life Sciences*, Vol 49, 1583 (1991), yielding [$^{111}$In-DTPA$^0$-Pro$^1$, Tyr$^4$] bombesin having a specific activity of 100 MBq/Lg.

Example 4

Gastrin releasing peptide receptor has high affinity for the 14 amino acid peptide bombesin. A bombesin analog, [$^{111}$In-DTPA$^0$, Pro$^1$, Tyr$^4$] bombesin, showed intact high affinity to the bombesin receptor, and agonistic activities on bombesin stimulated prolactin secretion on 7315b cells with an IC50 of 8 nM. After labeling with IN-111 up to a level of 100 Mbq per jj. g, the radioligand was radiochemically stable (>95%) for 2 h, as revealed by HPLC. In rats high and specific uptake was found in pancreas and tissues of the GI tract. Uptake of radioactivity could be blocked by iv coinjection of 100 ug Tyr4bombesin with the radioligand, but not when administered 1 h after the radioligand, indicating its internalization. A bell shaped function between injected mass and % ID per g bombesin receptor positive tissues was found at =0.025–0.1 pLg. Dynamic gamma camera showed rapid clearance of radioactivity from the blood compartment, renal uptake and urinary excretion: 35% in 1 h, 70% in 20 h with a total body retention of 10%. Specific uptake in the bombesin receptor positive prolactinoma 7315b inoculated on female Lewis rats was found and could also be visualized by scintigraphy. The residence time of radioactivity was in accordance with similar DTPA conjugated peptides. Thus, the radioligand [$^{111}$In-DTPA$^0$, Pro$^1$, Tyr$^4$] bombesin is suitable for scintigraphy of bombesin receptors in vivo.

TABLE 2

Tissue RA in % ID/g at 48 h after injection of 0.01–0.05 g of [$^{111}$In-DTPA$^0$, Pro$^1$, Tyr$^4$]bombesin labeled with 2 MBq In-111 in rats (n ≥ 3) and ratio vs. blood ( )

| µg | Pancreas | Colon | Stomach | Adrenal | Blood |
|---|---|---|---|---|---|
| 0.01 | 1.0(1210) | 0.072(85) | 0.035(40) | 0.029(34) | 0.0009 |
| 0.025 | 1.2(1217) | 0.063(64) | 0.065(64) | 0.030(30) | 0.0010 |
| 0.1 | 0.72(856) | 0.061(73) | 0.042(50) | 0.022(26) | 0.0009 |
| 0.5 | 0.43(574) | 0.036(52) | 0.036(50) | 0.014(18) | 0.0008 |

What is claimed is:

1. A pharmaceutical composition for targeting a selected biological site, the composition comprising:

a peptide $AA_1$-Gln-$AA_3$-Leu-Gly-Asn-Gln-Trp-Ala-Val-Gly-His-Leu-Met-NH2 wherein $AA_1$ is a cyclic amino acid of the formula wherein n=0 to 5;

wherein AA₃ is selected from the group consisting of Arg,

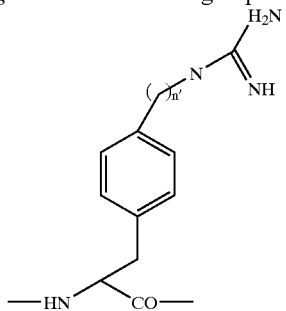

wherein n'=0 to 2, and

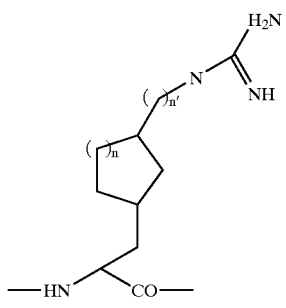

wherein n=1 to 3 and n'=0 to 3.

2. The composition according to claim 1 wherein AA₁ is selected from the group consisting of Pro, Pip, hPip, Moc and Mtc, and AA₃ is selected from the group consisting of Arg, gPhe, gmPhe, gePhe, gCpa, gmCpa, gpCpa, gCha, gmCha, geCha, gpCha, gChpa, gmChpa, geChpa and gpChpa.

3. The composition according to claim 1 further comprising an additional N-terminal amino acid residue or residues selected from the group consisting of L-His, D-His, L-His-Asp, and D-His-Asp.

4. The composition according to claim 1 wherein the cyclic ring further includes a heteroatom selected from the group consisting of O, S and N—R, wherein R=$C_1$ to $C_6$ normal or branched.

5. The composition according to claim 1 wherein the —CO group of AA₁ is replaced by an alkyl spacer wherein n=0 to 10 and a reactive group selected from the group consisting of COOH, NCS, NCO, and OCOX, wherein X is a reactive moiety.

6. The composition according to claim 1 further including a diagnostic or therapeutic radionuclide coupled to the peptide by a chelating agent.

7. The composition according to claim 6 wherein the diagnostic radionuclide is selected from the group consisting of $^{133m}$In, $^{99m}$Tc, $^{67}$Ga, $^{52}$Fe, $^{68}$Ga, $^{72}$As, $^{111}$In, $^{97}$Ru, $^{203}$Pb, $^{62}$Cu, $^{64}$Cu, $^{51}$Cr, $^{52m}$Mn, $^{157}$Gd, $^{123}$I, $^{124}$I, $^{131}$I, $^{75}$Br, $^{76}$Br, $^{77}$Br, and $^{82}$Br.

8. The composition according to claim 6 wherein the therapeutic radionuclide is selected from the group consisting of include $^{186}$Re, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{188}$Re, $^{77}$As, $^{166}$Dy, $^{166}$Ho, $^{149}$Pm, $^{151}$Pm, $^{153}$Sm, $^{159}$Gd, $^{172}$Tm, $^{169}$Yb, $^{175}$Yb, $^{177}$Lu, $^{105}$Rh, $^{111}$Ag, $^{131}$I, $^{129}$I and $^{177m}$Sn.

9. The composition according to claim 6 wherein the chelating agent is selected from the group consisting of DTPA, DTPA', DOTA and $N_tS_{4-t}$, wherein t=2–4.

10. A kit for the diagnosis of breast or prostate tumors or metastases of such tumors in a human comprising:

(a) a peptide AA₁-Gln-AA₃-Leu-Gly-Asn-Gln-Trp-Ala-Val-Gly-His-Leu-Met-NH2 wherein AA₁ is a cyclic amino acid of the formula

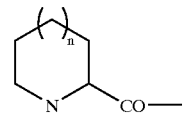

wherein n=0 to 5;

wherein AA₃ is selected from the group consisting of Arg,

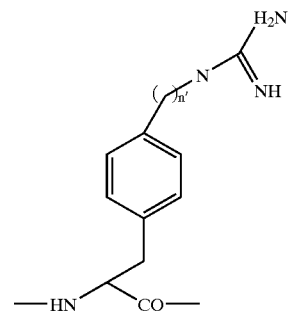

wherein n'=0 to 2, and

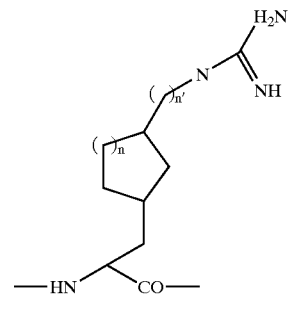

wherein n=1 to 3 and n'=0 to 3;

(b) a radioisotope; and (c) adjuvants suitable for administering the resultant combination to human.

11. A composition for the diagnosis of breast or prostate tumors or metastases of such tumors in a human comprising:

(a) the peptide according to claim 10; and (b) adjuvants suitable for administering the radiolabeled peptide to a human.

12. A method of diagnosis breast or prostate tumors or metastases of such tumors in a human patient comprising:

(a) administering to the patient a composition including a diagnostic amount of the peptide according to claim 10; and (b) externally imaging at least a portion of the patient to determine the location of localized radiation from the radiolabeled peptide.

13. A kit for the treatment of breast or prostate tumors or metastases of such tumors in a human comprising:

(a) a peptide AA$_1$-Gln-AA$_3$-Leu-Gly-Asn-Gln-Trp-Ala-Val-Gly-His-Leu-Met-NH2 wherein AA$_1$ is a cyclic amino acid of the formula

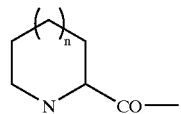

wherein n=0 to 5;

wherein AA$_3$ is selected from the group consisting of Arg,

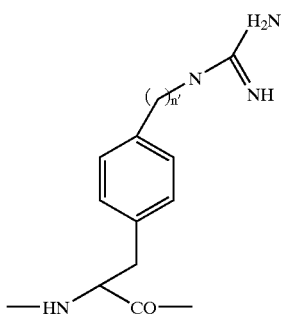

wherein n'=0 to 2, and

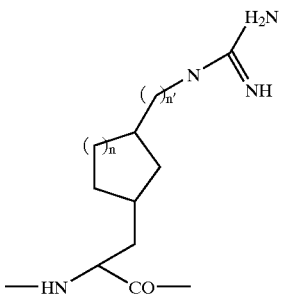

wherein n=1 to 3 and n'=0 to 3;
(b) a radioisotope: and
(c) adjuvants suitable for binding the radioisotope to the peptide and administering the resultant combination to a human.

14. A composition for the treatment of breast or prostate tumors or metastases of such tumors in a human comprising:
(a) the peptide according to claim 13; and
(b) adjuvants suitable for administering the radiolabeled peptide to a human.

15. A method of treating a breast or prostate tumor or metastases of such a tumor in a human patient comprising administering to the patient a composition including a therapeutic amount of the peptide according to claim 13.

* * * * *

UNITED STATES PATENT AND TRADEMARK OFFICE
CERTIFICATE OF CORRECTION

PATENT NO.    : 6,866,837 B2
DATED         : March 15, 2005
INVENTOR(S)   : Jean-Claude Reubi et al.

It is certified that error appears in the above-identified patent and that said Letters Patent is hereby corrected as shown below:

Column 4,
Line 23, delete "Metl4" and replace with -- Met14 --;

Column 8,
Line 3, delete "ge-Gha" and replace with -- ge-Cha --;
SEQ ID NOS: 11, 23, 24, 26, 28 and 29, delete "DPTA" and replace with -- DTPA --;
SEQ ID NO: 25, delete "TrP" and replace with -- Trp --;
SEQ ID NO: 28, delete "Try" and replace with -- Tyr --;

Column 9,
SEQ ID NOS: 30, 31, 32, 33, 34, 35, 36, 37, 38, 42, 43, 44, 45, 46, 48, 49, 50, 51, 52, 53, 54, 55, 56, 57, 58, 59, 60, 61, 62, 63, 64, 65, 66 and 67, delete "DPTA" and replace with -- DTPA --;

Column 11,
SEQ ID NOS: 68, 69, 70, 71, 72, 73, 74, 75, 76, 77, 78, 79, 80, 81, 82, 83, 84 and 86, delete "DPTA" and replace with -- DTPA --;
SEQ ID NO: 86, delete "Try" and replace with -- Tyr --;
Line 45, delete "$^{188}$Rd" and replace with -- $^{188}$Re --;

Column 12,
Line 38, delete "hydroxyethyidiamine" and replace with -- hydroxyethyldiamine --;

Column 16,
Line 17, delete "mmol/I" and replace with -- mmol/1 --;

UNITED STATES PATENT AND TRADEMARK OFFICE
CERTIFICATE OF CORRECTION

PATENT NO. : 6,866,837 B2
DATED : March 15, 2005
INVENTOR(S) : Jean-Claude Reubi et al.

It is certified that error appears in the above-identified patent and that said Letters Patent is hereby corrected as shown below:

<u>Column 78,</u>
Line 50, prior to the word "human" insert -- a --;
Line 57, delete "diagnosis" and replace with -- diagnosing --.

Signed and Sealed this

Eighteenth Day of October, 2005

JON W. DUDAS
*Director of the United States Patent and Trademark Office*

UNITED STATES PATENT AND TRADEMARK OFFICE
CERTIFICATE OF CORRECTION

PATENT NO. : 6,866,837 B2  Page 1 of 2
APPLICATION NO. : 10/248668
DATED : March 15, 2005
INVENTOR(S) : Jean-Claude Reubi et al.

It is certified that error appears in the above-identified patent and that said Letters Patent is hereby corrected as shown below:

Col. 2, line 53, delete "&commat" and replace with - - @ - -
Col. 2, line 54, delete "&commat" and replace with - - @ - -
Col. 3, line 24, delete "&commat" and replace with - - @ - -
Col. 4, line 23, delete "Metl4" and replace with - - Met14 - -
Col. 8, line 3, delete "ge-Gha" and replace with - - ge-Cha - -
Col. 8, SEQ ID NO: 11, delete "DPTA" and replace with - - DTPA - - ;
Col. 8, SEQ ID NO: 23, delete "DPTA" and replace with - - DTPA - - ;
Col. 8, SEQ ID NO: 24, delete "DPTA" and replace with - - DTPA - - ;
Col. 8, SEQ ID NO: 25, delete "TrP" and replace with - - Trp - - ;
Col. 8, SEQ ID NO: 26, delete "DPTA" and replace with - - DTPA - - ;
Col. 8, SEQ ID NO: 28, delete "DPTA" and replace with - - DTPA - - ;
Col. 8, SEQ ID NO: 28, delete "Try" and replace with - - Tyr - - ;
Col. 8, SEQ ID NO: 29, delete "DPTA" and replace with - - DTPA - - ;
Col. 9, SEQ ID NO: 30, delete "DPTA" and replace with - - DTPA - - ;
Col. 9, SEQ ID NO: 31, delete "DPTA" and replace with - - DTPA - - ;
Col. 9, SEQ ID NO: 32, delete "DPTA" and replace with - - DTPA - - ;
Col. 9, SEQ ID NO: 33, delete "DPTA" and replace with - - DTPA - - ;
Col. 9, SEQ ID NO: 34, delete "DPTA" and replace with - - DTPA - - ;
Col. 9, SEQ ID NO: 35, delete "DPTA" and replace with - - DTPA - - ;
Col. 9, SEQ ID NO: 36, delete "DPTA" and replace with - - DTPA - - ;
Col. 9, SEQ ID NO: 37, delete "DPTA" and replace with - - DTPA - - ;
Col. 9, SEQ ID NO: 38, delete "DPTA" and replace with - - DTPA - - ;
Col. 9, SEQ ID NO: 42, delete "DPTA" and replace with - - DTPA - - ;
Col. 9, SEQ ID NO: 43, delete "DPTA" and replace with - - DTPA - - ;
Col. 9, SEQ ID NO: 44, delete "DPTA" and replace with - - DTPA - - ;
Col. 9, SEQ ID NO: 45, delete "DPTA" and replace with - - DTPA - - ;
Col. 9, SEQ ID NO: 46 delete "DPTA" and replace with - - DTPA - - ;
Col. 9, SEQ ID NO: 48, delete "DPTA" and replace with - - DTPA - - ;
Col. 9, SEQ ID NO: 49, delete "DPTA" and replace with - - DTPA - - ;

UNITED STATES PATENT AND TRADEMARK OFFICE
CERTIFICATE OF CORRECTION

PATENT NO. : 6,866,837 B2
APPLICATION NO. : 10/248668
DATED : March 15, 2005
INVENTOR(S) : Jean-Claude Reubi et al.

It is certified that error appears in the above-identified patent and that said Letters Patent is hereby corrected as shown below:

Col. 9, SEQ ID NO: 50, delete "DPTA" and replace with - - DTPA - - ;
Col. 9, SEQ ID NO: 51, delete "DPTA" and replace with - - DTPA - - ;
Col. 9, SEQ ID NO: 52, delete "DPTA" and replace with - - DTPA - - ;
Col. 9, SEQ ID NO: 53, delete "DPTA" and replace with - - DTPA - - ;
Col. 9, SEQ ID NO: 54, delete "DPTA" and replace with - - DTPA - - ;

Signed and Sealed this

Twelfth Day of September, 2006

JON W. DUDAS
*Director of the United States Patent and Trademark Office*

SEQUENCE LISTING

<160> NUMBER OF SEQ ID NOS: 87

<210> SEQ ID NO 1
<211> LENGTH: 14
<212> TYPE: PRT
<213> ORGANISM: Bombina orientalis
<220> FEATURE:
<221> NAME/KEY: SITE
<222> LOCATION: (1)
<223> OTHER INFORMATION: Xaa is pyroglutamyl (pGlu).
<220> FEATURE:
<221> NAME/KEY: SITE
<222> LOCATION: (14)
<223> OTHER INFORMATION: Xaa is Met ending with an amide (Met-NH2).

<400> SEQUENCE: 1

Xaa Gln Arg Leu Gly Asn Gln Trp Ala Val Gly His Leu Xaa
 1               5                  10

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:Bombesin
      analog.

<400> SEQUENCE: 2

Trp Ala Val Gly His Leu
 1               5

```
<210> SEQ ID NO 3
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pyroglutamyl (pGlu).
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 3

Xaa Gln Lys Leu Gly Asn Gln Trp Ala Val Gly His Leu Xaa
 1               5                  10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence:Bombesin
      analog.

<400> SEQUENCE: 4

Gln Trp Ala Val Gly His Leu Met
 1               5

<210> SEQ ID NO 5
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is a cyclic amino acid.
<220> FEATURE:
<221> NAME/KEY: SITE
<222> LOCATION: (3)
<223> OTHER INFORMATION: Xaa is a chemical equivalent of arginine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 5

Xaa Gln Xaa Tyr Gly Asn Gln Trp Ala Val Gly His Leu Xaa
 1               5                  10

<210> SEQ ID NO 6
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pyroglutamyl (pGlu).
<220> FEATURE:
<221> NAME/KEY: SITE
<222> LOCATION: (14)
<223> OTHER INFORMATION: Xaa is Met ending in an amide (Met-NH2).
<220> FEATURE:
<223> OTHER INFORMATION: Description of Artificial Sequence:Bombesin
      analog.

<400> SEQUENCE: 6
```

Xaa Gln Arg Tyr Gly Asn Gln Trp Ala Val Gly His Leu Xaa
 1               5                   10

<210> SEQ ID NO 7
<211> LENGTH: 15
<212> TYPE: PRT
<213> ORGANISM: Artificial Sequence
<220> FEATURE:
<221> NAME/KEY: SITE
<222> LOCATION: (1)
<223> OTHER INFORMATION: Xaa is L- or D-His.
<220> FEATURE:
<221> NAME/KEY: SITE
<222> LOCATION: (2)
<223> OTHER INFORMATION: Xaa (shown as AA1 in the specification) is a
      cyclic amino acid residue.
<220> FEATURE:
<221> NAME/KEY: SITE
<222> LOCATION: (4)
<223> OTHER INFORMATION: Xaa (shown as AA3 in the specification) is any
      L or D amino acid residue.
<220> FEATURE:
<221> NAME/KEY: SITE
<222> LOCATION: (5)
<223> OTHER INFORMATION: Xaa (shown as AA4 in the specification) is any
      L or D amino acid residue.
<220> FEATURE:
<221> NAME/KEY: SITE
<222> LOCATION: (15)
<223> OTHER INFORMATION: Xaa (shown as AA14 in the specification) is
      any D or L amino acid residue and ends with an amide (Xaa-NH2).
<220> FEATURE:
<223> OTHER INFORMATION: Description of Artificial Sequence:Bombesin
      analog.

<400> SEQUENCE: 7

Xaa Xaa Gln Xaa Xaa Gly Asn Gln Trp Ala Val Gly His Leu Xaa
 1               5                   10                  15

<210> SEQ ID NO 8
<211> LENGTH: 16
<212> TYPE: PRT
<213> ORGANISM: Artificial Sequence
<220> FEATURE:
<221> NAME/KEY: SITE
<222> LOCATION: (1)
<223> OTHER INFORMATION: Xaa is L- or D-His.
<220> FEATURE:
<221> NAME/KEY: SITE
<222> LOCATION: (2)
<223> OTHER INFORMATION: Xaa is beta-Asp.
<220> FEATURE:
<221> NAME/KEY: SITE
<222> LOCATION: (3)
<223> OTHER INFORMATION: Xaa (shown as AA1 in the specification) is a
      cyclic amino acid residue.
<220> FEATURE:
<221> NAME/KEY: SITE
<222> LOCATION: (5)
<223> OTHER INFORMATION: Xaa (shown as AA3 in the specification) is any
      D or L amino acid residue.
<220> FEATURE:
<221> NAME/KEY: SITE
<222> LOCATION: (6)
<223> OTHER INFORMATION: Xaa (shown as AA4 in the specification) is any
      D or L amino acid residue.
<220> FEATURE:
<221> NAME/KEY: SITE
<222> LOCATION: (16)
<223> OTHER INFORMATION: Xaa (shown as AA14 in the specification) is
      any D or L amino acid residue and ends with an amide (Xaa-NH2).
<220> FEATURE:
<223> OTHER INFORMATION: Description of Artificial Sequence:Bombesin
      analog.

```
<400> SEQUENCE: 8

Xaa Xaa Xaa Gln Xaa Xaa Gly Asn Gln Trp Ala Val Gly His Leu Xaa
 1               5                  10                  15

<210> SEQ ID NO 9
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pyroglutamyl (pGlu) with DTPA
      (diethylene triamine penta-acetic acid).
<220> FEATURE:
<221> NAME/KEY: SITE
<222> LOCATION: (14)
<223> OTHER INFORMATION: Xaa is Met ending in an amide (Met-NH2).
<220> FEATURE:
<223> OTHER INFORMATION: Description of Artificial Sequence:Bombesin
      analog.

<400> SEQUENCE: 9

Xaa Gln Arg Tyr Gly Asn Gln Trp Ala Val Gly His Leu Xaa
 1               5                  10

<210> SEQ ID NO 10
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 10

Xaa Gln Arg Tyr Gly Asn Gln Trp Ala Val Gly His Leu Xaa
 1               5                  10

<210> SEQ ID NO 11
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (14)
<223> OTHER INFORMATION: Xaa is Met ending in an amide (Met-NH2).
<220> FEATURE:
<223> OTHER INFORMATION: Description of Artificial Sequence:Bombesin
      analog.

<400> SEQUENCE: 11

Xaa Gln Arg Tyr Gly Asn Gln Trp Ala Val Gly His Leu Xaa
 1               5                  10

<210> SEQ ID NO 12
<211> LENGTH: 14
<212> TYPE: PRT
<213> ORGANISM: Artificial Sequence
```

```
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (14)
<223> OTHER INFORMATION: Xaa is Met ending in an amide (Met-NH2).
<220> FEATURE:
<223> OTHER INFORMATION: Description of Artificial Sequence:Bombesin
      analog.

<400> SEQUENCE: 12

Xaa Gln Arg Tyr Gly Asn Gln Trp Ala Val Gly His Leu Xaa
 1               5                  10

<210> SEQ ID NO 13
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (14)
<223> OTHER INFORMATION: Xaa is norleucine ending with an amide
      (Nle-NH2).
<220> FEATURE:
<223> OTHER INFORMATION: Description of Artificial Sequence:Bombesin
      analog.

<400> SEQUENCE: 13

Xaa Gln Arg Tyr Gly Asn Gln Trp Ala Val Gly His Leu Xaa
 1               5                  10

<210> SEQ ID NO 14
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (14)
<223> OTHER INFORMATION: Xaa is norleucine ending in an amide
      (Nle-NH2).
<220> FEATURE:
<223> OTHER INFORMATION: Description of Artificial Sequence:Bombesin
      analog.

<400> SEQUENCE: 14

Xaa Gln Arg Tyr Gly Asn Gln Trp Ala Val Gly His Leu Xaa
 1               5                  10

<210> SEQ ID NO 15
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (14)
```

-continued

```
<223> OTHER INFORMATION: Xaa is norleucine ending with an amide
      (Nle-NH2).
<220> FEATURE:
<223> OTHER INFORMATION: Description of Artificial Sequence:Bombesin
      analog.

<400> SEQUENCE: 15

Xaa Gln Arg Tyr Gly Asn Gln Trp Ala Val Gly His Leu Xaa
 1               5                  10

<210> SEQ ID NO 16
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<223> OTHER INFORMATION: Description of Artificial Sequence:Bombesin
      analog.
<220> FEATURE:
<221> NAME/KEY: SITE
<222> LOCATION: (14)
<223> OTHER INFORMATION: Xaa is Met ending in an amide (Met-NH2).

<400> SEQUENCE: 16

Xaa Gln Arg Tyr Gly Asn Gln Trp Ala Val Gly His Leu Xaa
 1               5                  10

<210> SEQ ID NO 17
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Mtc (thiomorpholino 2-carboxylic acid)
      with DTPA (diethylene triamine penta-acetic acid).
<220> FEATURE:
<221> NAME/KEY: SITE
<222> LOCATION: (14)
<223> OTHER INFORMATION: Xaa is Met ending in an amide (Met-NH2).
<220> FEATURE:
<223> OTHER INFORMATION: Description of Artificial Sequence:Bombesin
      analog.

<400> SEQUENCE: 17

Xaa Gln Arg Tyr Gly Asn Gln Trp Ala Val Gly His Leu Xaa
 1               5                  10

<210> SEQ ID NO 18
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (3)
<223> OTHER INFORMATION: Xaa is guanidinophenylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.
```

```
<400> SEQUENCE: 18

Xaa Gln Xaa Tyr Gly Asn Gln Trp Ala Val Gly His Leu Xaa
 1               5                   10

<210> SEQ ID NO 19
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (3)
<223> OTHER INFORMATION: Xaa is guanidinomethylphenylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 19

Xaa Gln Xaa Tyr Gly Asn Gln Trp Ala Val Gly His Leu Xaa
 1               5                   10

<210> SEQ ID NO 20
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (3)
<223> OTHER INFORMATION: Xaa is guanidinoethylphenylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 20

Xaa Gln Xaa Tyr Gly Asn Gln Trp Ala Val Gly His Leu Xaa
 1               5                   10

<210> SEQ ID NO 21
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinophenylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
```

-continued analog.

<400> SEQUENCE: 21

Xaa Gln Xaa Tyr Gly Asn Gln Trp Ala Val Gly His Leu Xaa
 1               5                  10

<210> SEQ ID NO 22
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinomethylphenylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 22

Xaa Gln Xaa Tyr Gly Asn Gln Trp Ala Val Gly His Leu Xaa
 1               5                  10

<210> SEQ ID NO 23
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinoethylphenylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 23

Xaa Gln Xaa Tyr Gly Asn Gln Trp Ala Val Gly His Leu Xaa
 1               5                  10

<210> SEQ ID NO 24
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinophenylalanine.
<220> FEATURE:
<221> NAME/KEY: SITE
<222> LOCATION: (14)
<223> OTHER INFORMATION: Xaa is Met ending with an amide (Met-NH2).

```
<220> FEATURE:
<223> OTHER INFORMATION: Description of Artificial Sequence:Bombesin
      analog.

<400> SEQUENCE: 24

Xaa Gln Xaa Tyr Gly Asn Gln Trp Ala Val Gly His Leu Xaa
 1               5                  10

<210> SEQ ID NO 25
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
<223> OTHER INFORMATION: Xaa is guanidinomethylphenylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 25

Xaa Gln Xaa Tyr Gly Asn Gln Trp Ala Val Gly His Leu Xaa
 1               5                  10

<210> SEQ ID NO 26
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Mtc (thiomorpholino 2-carboxylic acid)
      with DTPA (diethylene triamine penta-acetic acid).
<220> FEATURE:
<221> NAME/KEY: SITE
<222> LOCATION: (3)
<223> OTHER INFORMATION: Xaa is guanidinoethylphenylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 26

Xaa Gln Xaa Tyr Gly Asn Gln Trp Ala Val Gly His Leu Xaa
 1               5                  10

<210> SEQ ID NO 27
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (3)
<223> OTHER INFORMATION: Xaa is guanidinocyclopentylalanine.
<220> FEATURE:
<221> NAME/KEY: SITE
```

```
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 27

Xaa Gln Xaa Tyr Gly Asn Gln Trp Ala Val Gly His Leu Xaa
 1               5                  10

<210> SEQ ID NO 28
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (3)
<223> OTHER INFORMATION: Xaa is guanidinomethylcyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 28

Xaa Gln Xaa Tyr Gly Asn Gln Trp Ala Val Gly His Leu Xaa
 1               5                  10

<210> SEQ ID NO 29
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (3)
<223> OTHER INFORMATION: Xaa is guanidinoethylcyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 29

Xaa Gln Xaa Tyr Gly Asn Gln Trp Ala Val Gly His Leu Xaa
 1               5                  10

<210> SEQ ID NO 30
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (3)
<223> OTHER INFORMATION: Xaa is guanidinopropylcyclopentylalanine.
```

```
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 30

Xaa Gln Xaa Tyr Gly Asn Gln Trp Ala Val Gly His Leu Xaa
 1               5                  10

<210> SEQ ID NO 31
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (3)
<223> OTHER INFORMATION: Xaa is guanidinocyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 31

Xaa Gln Xaa Tyr Gly Asn Gln Trp Ala Val Gly His Leu Xaa
 1               5                  10

<210> SEQ ID NO 32
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (3)
<223> OTHER INFORMATION: Xaa is guanidinomethylcyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 32

Xaa Gln Xaa Tyr Gly Asn Gln Trp Ala Val Gly His Leu Xaa
 1               5                  10

<210> SEQ ID NO 33
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
```

```
<222> LOCATION: (3)
<223> OTHER INFORMATION: Xaa is guanidinoethylcyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 33

Xaa Gln Xaa Tyr Gly Asn Gln Trp Ala Val Gly His Leu Xaa
 1               5                  10

<210> SEQ ID NO 34
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (3)
<223> OTHER INFORMATION: Xaa is guanidinopropylcyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 34

Xaa Gln Xaa Tyr Gly Asn Gln Trp Ala Val Gly His Leu Xaa
 1               5                  10

<210> SEQ ID NO 35
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (3)
<223> OTHER INFORMATION: Xaa is guanidinocycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 35

Xaa Gln Xaa Tyr Gly Asn Gln Trp Ala Val Gly His Leu Xaa
 1               5                  10

<210> SEQ ID NO 36
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
```

```
<220> FEATURE:
<221> NAME/KEY: SITE
<222> LOCATION: (3)
<223> OTHER INFORMATION: Xaa is guanidinomethylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 36

Xaa Gln Xaa Tyr Gly Asn Gln Trp Ala Val Gly His Leu Xaa
 1               5                   10

<210> SEQ ID NO 37
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (3)
<223> OTHER INFORMATION: Xaa is guanidinoethylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 37

Xaa Gln Xaa Tyr Gly Asn Gln Trp Ala Val Gly His Leu Xaa
 1               5                   10

<210> SEQ ID NO 38
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pro with DTPA (diethylene triamine
      penta-acetic acid).
<220> FEATURE:
<221> NAME/KEY: SITE
<222> LOCATION: (3)
<223> OTHER INFORMATION: Xaa is guanidinopropylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 38

Xaa Gln Xaa Tyr Gly Asn Gln Trp Ala Val Gly His Leu Xaa
 1               5                   10

<210> SEQ ID NO 39
<211> LENGTH: 14
<212> TYPE: PRT
<213> ORGANISM: Artificial Sequence
<220> FEATURE:
<221> NAME/KEY: SITE
<222> LOCATION: (1)
```

<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinocyclopentylalaninine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 39

Xaa Gln Xaa Tyr Gly Asn Gln Trp Ala Val Gly His Leu Xaa
 1               5                  10

<210> SEQ ID NO 40
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinomethylcyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 40

Xaa Gln Xaa Tyr Gly Asn Gln Trp Ala Val Gly His Leu Xaa
 1               5                  10

<210> SEQ ID NO 41
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinoethylcyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 41

Xaa Gln Xaa Tyr Gly Asn Gln Trp Ala Val Gly His Leu Xaa
 1               5                  10

<210> SEQ ID NO 42
<211> LENGTH: 14
<212> TYPE: PRT
<213> ORGANISM: Artificial Sequence
<220> FEATURE:

```
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinopropylcyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 42

Xaa Gln Xaa Tyr Gly Asn Gln Trp Ala Val Gly His Leu Xaa
 1               5                  10

<210> SEQ ID NO 43
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinocyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 43

Xaa Gln Xaa Tyr Gly Asn Gln Trp Ala Val Gly His Leu Xaa
 1               5                  10

<210> SEQ ID NO 44
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinomethylcyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 44

Xaa Gln Xaa Tyr Gly Asn Gln Trp Ala Val Gly His Leu Xaa
 1               5                  10

<210> SEQ ID NO 45
<211> LENGTH: 14
<212> TYPE: PRT
```

```
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinoethylcyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 45

Xaa Gln Xaa Tyr Gly Asn Gln Trp Ala Val Gly His Leu Xaa
 1               5                  10

<210> SEQ ID NO 46
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinopropylcyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 46

Xaa Gln Xaa Tyr Gly Asn Gln Trp Ala Val Gly His Leu Xaa
 1               5                  10

<210> SEQ ID NO 47
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinocycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 47

Xaa Gln Xaa Tyr Gly Asn Gln Trp Ala Val Gly His Leu Xaa
 1               5                  10

<210> SEQ ID NO 48
```

```
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinomethylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 48

Xaa Gln Xaa Tyr Gly Asn Gln Trp Ala Val Gly His Leu Xaa
  1               5                  10

<210> SEQ ID NO 49
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinoethylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 49

Xaa Gln Xaa Tyr Gly Asn Gln Trp Ala Val Gly His Leu Xaa
  1               5                  10

<210> SEQ ID NO 50
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Pip (pipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinopropylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 50

Xaa Gln Xaa Tyr Gly Asn Gln Trp Ala Val Gly His Leu Xaa
  1               5                  10
```

```
<210> SEQ ID NO 51
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinocyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 51

Xaa Gln Xaa Tyr Gly Asn Gln Trp Ala Val Gly His Leu Xaa
 1               5                  10

<210> SEQ ID NO 52
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinomethylcyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 52

Xaa Gln Xaa Tyr Gly Asn Gln Trp Ala Val Gly His Leu Xaa
 1               5                  10

<210> SEQ ID NO 53
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinoethylcyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 53

Xaa Gln Xaa Tyr Gly Asn Gln Trp Ala Val Gly His Leu Xaa
```

```
                1               5                   10
```

<210> SEQ ID NO 54
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinopropylcyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 54

Xaa Gln Xaa Tyr Gly Asn Gln Trp Ala Val Gly His Leu Xaa
 1               5                   10

<210> SEQ ID NO 55
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinocyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 55

Xaa Gln Xaa Tyr Gly Asn Gln Trp Ala Val Gly His Leu Xaa
 1               5                   10

<210> SEQ ID NO 56
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinomethylcyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 56

```
Xaa Gln Xaa Tyr Gly Asn Gln Trp Ala Val Gly His Leu Xaa
 1               5                   10
```

<210> SEQ ID NO 57
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinoethylcyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 57

```
Xaa Gln Xaa Tyr Gly Asn Gln Trp Ala Val Gly His Leu Xaa
 1               5                   10
```

<210> SEQ ID NO 58
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinopropylcyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 58

```
Xaa Gln Xaa Tyr Gly Asn Gln Trp Ala Val Gly His Leu Xaa
 1               5                   10
```

<210> SEQ ID NO 59
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinocycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

-continued

```
<400> SEQUENCE: 59

Xaa Gln Xaa Tyr Gly Asn Gln Trp Ala Val Gly His Leu Xaa
 1               5                  10

<210> SEQ ID NO 60
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinomethylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 60

Xaa Gln Xaa Tyr Gly Asn Gln Trp Ala Val Gly His Leu Xaa
 1               5                  10

<210> SEQ ID NO 61
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinoethylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 61

Xaa Gln Xaa Tyr Gly Asn Gln Trp Ala Val Gly His Leu Xaa
 1               5                  10

<210> SEQ ID NO 62
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is hPip (homopipecolic acid) with DTPA
      (diethylene triamine penta-acetic acid).
<220> FEATURE:
<221> NAME/KEY: SITE
<222> LOCATION: (3)
<223> OTHER INFORMATION: Xaa is guanidinopropylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
```

```
<223> OTHER INFORMATION: Description of Artificial Sequence:Bombesin
      analog.

<400> SEQUENCE: 62

Xaa Gln Xaa Tyr Gly Asn Gln Trp Ala Val Gly His Leu Xaa
 1               5                  10

<210> SEQ ID NO 63
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
<223> OTHER INFORMATION: Xaa is guanidinocyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 63

Xaa Gln Xaa Tyr Gly Asn Gln Trp Ala Val Gly His Leu Xaa
 1               5                  10

<210> SEQ ID NO 64
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
<223> OTHER INFORMATION: Xaa is guanidinomethylcyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 64

Xaa Gln Xaa Tyr Gly Asn Gln Trp Ala Val Gly His Leu Xaa
 1               5                  10

<210> SEQ ID NO 65
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
<223> OTHER INFORMATION: Xaa is guanidinoethylcyclopentylalanine.
<220> FEATURE:
<221> NAME/KEY: SITE
<222> LOCATION: (14)
```

```
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 65

Xaa Gln Xaa Tyr Gly Asn Gln Trp Ala Val Gly His Leu Xaa
 1               5                  10

<210> SEQ ID NO 66
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
<223> OTHER INFORMATION: Xaa is guanidinopropylcyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 66

Xaa Gln Xaa Tyr Gly Asn Gln Trp Ala Val Gly His Leu Xaa
 1               5                  10

<210> SEQ ID NO 67
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
<223> OTHER INFORMATION: Xaa is guanidinocyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 67

Xaa Gln Xaa Tyr Gly Asn Gln Trp Ala Val Gly His Leu Xaa
 1               5                  10

<210> SEQ ID NO 68
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
<223> OTHER INFORMATION: Xaa is guanidinomethylcyclohexylalanine.
<220> FEATURE:
```

```
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 68

Xaa Gln Xaa Tyr Gly Asn Gln Trp Ala Val Gly His Leu Xaa
 1               5                  10

<210> SEQ ID NO 69
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
<223> OTHER INFORMATION: Xaa is guanidinoethylcyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 69

Xaa Gln Xaa Tyr Gly Asn Gln Trp Ala Val Gly His Leu Xaa
 1               5                  10

<210> SEQ ID NO 70
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
<223> OTHER INFORMATION: Xaa is guanidinopropylcyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 70

Xaa Gln Xaa Tyr Gly Asn Gln Trp Ala Val Gly His Leu Xaa
 1               5                  10

<210> SEQ ID NO 71
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
```

<223> OTHER INFORMATION: Xaa is guanidinocycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 71

Xaa Gln Xaa Tyr Gly Asn Gln Trp Ala Val Gly His Leu Xaa
 1               5                  10

<210> SEQ ID NO 72
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
<223> OTHER INFORMATION: Xaa is guanidinomethylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 72

Xaa Gln Xaa Tyr Gly Asn Gln Trp Ala Val Gly His Leu Xaa
 1               5                  10

<210> SEQ ID NO 73
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
<223> OTHER INFORMATION: Xaa is guanidinoethylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 73

Xaa Gln Xaa Tyr Gly Asn Gln Trp Ala Val Gly His Leu Xaa
 1               5                  10

<210> SEQ ID NO 74
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:

```
<221> NAME/KEY: SITE
<222> LOCATION: (3)
<223> OTHER INFORMATION: Xaa is guanidinopropylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 74

Xaa Gln Xaa Tyr Gly Asn Gln Trp Ala Val Gly His Leu Xaa
 1               5                  10

<210> SEQ ID NO 75
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Mtc (thiomorpholino 2-carboxylic acid)
      with DTPA (diethylene triamine penta-acetic acid).
<220> FEATURE:
<221> NAME/KEY: SITE
<222> LOCATION: (3)
<223> OTHER INFORMATION: Xaa is guanidinocyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 75

Xaa Gln Xaa Tyr Gly Asn Gln Trp Ala Val Gly His Leu Xaa
 1               5                  10

<210> SEQ ID NO 76
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Mtc (thiomorpholino 2-carboxylic acid)
      with DTPA (diethylene triamine penta-acetic acid).
<220> FEATURE:
<221> NAME/KEY: SITE
<222> LOCATION: (3)
<223> OTHER INFORMATION: Xaa is guanidinomethylcyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 76

Xaa Gln Xaa Tyr Gly Asn Gln Trp Ala Val Gly His Leu Xaa
 1               5                  10

<210> SEQ ID NO 77
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Mtc (thiomorpholino 2-carboxylic acid)
``` with DTPA (diethylene triamine penta-acetic acid).
<220> FEATURE:
<221> NAME/KEY: SITE
<222> LOCATION: (3)
<223> OTHER INFORMATION: Xaa is guanidinoethylcyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
        analog.

<400> SEQUENCE: 77

Xaa Gln Xaa Tyr Gly Asn Gln Trp Ala Val Gly His Leu Xaa
 1               5                  10

<210> SEQ ID NO 78
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Mtc (thiomorpholino 2-carboxylic acid)
        with DTPA (diethylene triamine penta-acetic acid).
<220> FEATURE:
<221> NAME/KEY: SITE
<222> LOCATION: (3)
<223> OTHER INFORMATION: Xaa is guanidinopropylcyclopentylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
        analog.

<400> SEQUENCE: 78

Xaa Gln Xaa Tyr Gly Asn Gln Trp Ala Val Gly His Leu Xaa
 1               5                  10

<210> SEQ ID NO 79
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Mtc (thiomorpholino 2-carboxylic acid)
        with DTPA (diethylene triamine penta-acetic acid).
<220> FEATURE:
<221> NAME/KEY: SITE
<222> LOCATION: (3)
<223> OTHER INFORMATION: Xaa is guanidinocyclohexylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
        analog.

<400> SEQUENCE: 79

Xaa Gln Xaa Tyr Gly Asn Gln Trp Ala Val Gly His Leu Xaa
 1               5                  10

<210> SEQ ID NO 80
<211> LENGTH: 14
<212> TYPE: PRT
<213> ORGANISM: Artificial Sequence
<220> FEATURE:
<221> NAME/KEY: SITE

```
<222> LOCATION: (1)
<223> OTHER INFORMATION: Xaa is Mtc (thiomorpholino 2-carboxylic acid)
      with DTPA (di <210> SEQ ID NO 83
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Mtc (thiomorpholino 2-carboxylic acid)
      with DTPA (diethylene triamine penta-acetic acid).
<220> FEATURE:
<221> NAME/KEY: SITE
<222> LOCATION: (3)
<223> OTHER INFORMATION: Xaa is guanidinocycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 83

Xaa Gln Xaa Tyr Gly Asn Gln Trp Ala Val Gly His Leu Xaa
 1               5                  10

<210> SEQ ID NO 84
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
<223> OTHER INFORMATION: Xaa is guanidinomethylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 84

Xaa Gln Xaa Tyr Gly Asn Gln Trp Ala Val Gly His Leu Xaa
 1               5                  10

<210> SEQ ID NO 85
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)

```
<223> OTHER INFORMATION: Xaa is guanidinoethylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 85

Xaa Gln Xaa Tyr Gly Asn Gln Trp Ala Val Gly His Leu Xaa
 1               5                  10

<210> SEQ ID NO 86
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Moc (morpholino 2-carboxylic acid) with
      DTPA (diethylene triamine penta-acetic acid).
<220> FEATURE:
<221> NAME/KEY: SITE
<222> LOCATION: (3)
<223> OTHER INFORMATION: Xaa is guanidinopropylcycloheptylalanine.
<220> FEATURE:
<221> NAME/KEY: SITE
<222> LOCATION: (14)
<223> OTHER INFORMATION: Xaa is Met ending with an amide (Met-NH2).
<220> FEATURE:
<223> OTHER INFORMATION: Description of Artificial Sequence:Bombesin
      analog.

<400> SEQUENCE: 86

Xaa Gln Xaa Tyr Gly Asn Gln Trp Ala Val Gly His Leu Xaa
 1               5                  10

<210> SEQ ID NO 87
<211> LENGTH: 14
<212> TYPE: PRT
<213> ORGANISM: Artificial Sequence
<220> FEATURE:
<221> NAME/KEY: SITE
<222> LOCATION: (1)
<223> OTHER INFORMATION: Xaa is pyroglutamyl (pGlu).
<220> FEATURE:
<221> NAME/KEY: SITE
<222> LOCATION: (4)
<223> OTHER INFORMATION: Xaa is radioiodinated tyrosine.
<220> FEATURE:
<221> NAME/KEY: SITE
<222> LOCATION: (14)
<223> OTHER INFORMATION: Xaa is Met ending in an amide (Met-NH2).
<220> FEATURE:
<223> OTHER INFORMATION: Description of Artificial Sequence:Bombesin
      analog.

<400> SEQUENCE: 87

Xaa Gln Arg Xaa Gly Asn Gln Trp Ala Val Gly His Leu Xaa
 1               5                  10
```